(12) United States Patent
Farah et al.

(10) Patent No.: US 11,179,520 B2
(45) Date of Patent: Nov. 23, 2021

(54) SYRINGE

(71) Applicants: Samer E. Farah, New York, NY (US); Matthew Feinsod, Great Neck, NY (US)

(72) Inventors: Samer E. Farah, New York, NY (US); Matthew Feinsod, Great Neck, NY (US)

( * ) Notice: Subject to any disclaimer, the term of this patent is extended or adjusted under 35 U.S.C. 154(b) by 74 days.

(21) Appl. No.: 15/933,142

(22) Filed: Mar. 22, 2018

(65) Prior Publication Data

US 2018/0271701 A1 Sep. 27, 2018

Related U.S. Application Data

(60) Provisional application No. 62/475,048, filed on Mar. 22, 2017.

(51) Int. Cl.
*A61M 5/31* (2006.01)
*A61F 9/00* (2006.01)
(Continued)

(52) U.S. Cl.
CPC ....... *A61M 5/3137* (2013.01); *A61B 10/0045* (2013.01); *A61F 9/0008* (2013.01); *A61F 9/0017* (2013.01); *A61M 5/31511* (2013.01); *A61B 2010/0067* (2013.01); *A61B 2010/0077* (2013.01); *A61M 1/67* (2021.05); *A61M 5/3129* (2013.01); *A61M 5/31513* (2013.01); *A61M 2005/3131* (2013.01); *A61M 2202/0464* (2013.01); *A61M 2210/0612* (2013.01); *A61M 2210/0693* (2013.01)

(58) Field of Classification Search
CPC ........ A61B 10/0045; A61B 2010/0067; A61B 2010/0077; A61F 9/0017; A61F 9/0008; A61M 2210/0693; A61M 2210/0612; A61M 2010/0077; A61M 2202/0464; A61M 2005/3131; A61M 1/0009; A61M 5/31513; A61M 5/3137; A61M 5/3129
See application file for complete search history.

(56) References Cited

U.S. PATENT DOCUMENTS 4,364,388 A    12/1982  Cech
4,904,244 A *   2/1990  Harsh ................. A61M 5/3205
                                                                604/110

(Continued)

OTHER PUBLICATIONS

Allansmith et al., The diagnostic value of anterior chamber paracentesis in 14 cases of postoperative endophthalmitis. Trans Am Ophthalmol Soc. 1970;68:335-55.

(Continued)

*Primary Examiner* — William R Carpenter
(74) *Attorney, Agent, or Firm* — McCarter & English, LLP; David R. Burns

(57) ABSTRACT

This disclosure describes devices and methods used to inject or aspirate fluid into or from various regions of the human body, such as the anterior chamber of the eye. The disclosed devices and methods provide improvements over conventional devices and methods in that an operator can perform a procedure using the disclosed device without an assistant. The disclosed devices and methods allow one-handed injection or aspiration of fluid into or from body tissue, and provide means for controlling the volume of injected or aspirated fluid.

7 Claims, 10 Drawing Sheets

(51) Int. Cl.
*A61B 10/00* (2006.01)
*A61M 5/315* (2006.01)
*A61M 1/00* (2006.01)

(56) References Cited

U.S. PATENT DOCUMENTS

| | | | | |
|---|---|---|---|---|
| 4,950,265 | A * | 8/1990 | Taylor | A61B 10/0275 600/562 |
| 5,115,816 | A * | 5/1992 | Lee | A61M 5/1782 600/562 |
| 5,350,365 | A * | 9/1994 | De Godoy Moreira | A61B 17/8822 604/187 |
| 2004/0267206 | A1* | 12/2004 | Rimlinger | A61M 5/326 604/198 |
| 2007/0265573 | A1 | 11/2007 | Fojtik | |
| 2011/0046559 | A1* | 2/2011 | Lum | A61M 5/3137 604/189 |
| 2012/0123194 | A1 | 5/2012 | Beckman et al. | |
| 2014/0323984 | A1 | 10/2014 | Bruce et al. | |
| 2015/0032081 | A1 | 1/2015 | Fojtik | |

OTHER PUBLICATIONS

Arnavielle et al., Anterior chamber paracentesis in patients with acute elevation of intraocular pressure. Graefes Arch Clin Exp Ophthalmol. Mar. 2007;245(3):345-50.
Azuara-Blanco et al., Infectious keratitis in a paracentesis tract. Ophthalmic Surg Lasers. Apr. 1997;28(4):332-3.
Carnahan et al., Serial paracenteses in the management of acute elevations of intraocular pressure. Ophthalmology. Sep. 2002;109(9):1604-6.
Chern et al., Anterior Chamber Paracentesis. Ophthalmic Office Procedures: A Step-by-Step Approach. McGraw Hill, New York. Chapter 4, pp. 17-20, (2004).
Cheung et al., The safety of anterior chamber paracentesis in patients with uveitis Br J Ophthalmol. 2004;88:582-583.
De Boer et al., Analysis of ocular fluids for local antibody production in uveitis Br J Ophthalmol. Jun. 1995;79 (6):610-6.
De Boer et al., Serologic and polymerase chain reaction analysis of intraocular fluids in the diagnosis of infectious uveitis. Am J Ophthalmol. Jun. 1996;121(6):650-8.
Finger et al., Anterior chamber paracentesis cytology (cytospin technique) for the diagnosis of intraocular lymphoma. Br J Ophthalmol. Jun. 2006;90(6):690-2.
Grewal, A technique for paracentesis. Ophthalmic Surg. Jul. 1989;20(7):525.
Helbig et al., Bacterial endophthalmitis after anterior chamber paracentesis. Br J Ophthalmol. Sep. 1995;79(9):866.
Lam et al., Efficacy and safety of immediate anterior chamber paracentesis in the treatment of acute primary angle-closure glaucoma: a pilot study. Ophthalmology. Jan. 2002;109(1):64-70.
Lee et al., Multiple retinal hemorrhage following anterior chamber paracentesis in uveitic glaucoma. Korean J Ophthalmol. Jun. 2006;20(2):128-30.
Martola et al., Central and peripheral corneal thickness. A clinical study. Arch Ophthalmol. Jan. 1968;79(1):28-30.
May et al., An improved approach to aqueous paracentesis. Ophthalmic Surg. Nov. 1988;19(11):821-2.
O'Rourke et al., An aqueous paracentesis pipet. Ophthalmic Surg. Mar. 1991;22(3):166-7.
Pong, Anterior chamber paracentesis in patients with acute elevation of intraocular pressure. Graefes Arch Clin Exp Ophthalmol. Mar. 2008;246(3):463-4.
Robichon et al., Anterior Chamber Paracentesis in the Treatment of Acute Elevation of Intraocular Pressure. ARVO Annual Meeting. Investigative Ophthalmology & Visual Science. May 2005;46(13), Abstract 106.
Rumelt et al., Update on treatment of retinal arterial occlusions. Curr Opin Ophthalmol. Jun. 2003;14(3):139-41.
Sarabia Vision Specialists Group. Controlled anterior chamber paracentesis . . . Retrieved online at https://web.archive.org/web/20100414083939/http://www.sarabiavision.com:80/controlled-anterior-chamber-paracentesis-effective-for-acute-angle-closure-glaucoma/ 5 pages. Dec. 27, 2009.
Sawtelle, Acute Angle-Closure Glaucoma. Clinical Practice of Emergency Medicine, Sixth Edition. Allan B. Wolfson (Ed.), Wolters Klumer, Philadelphia. Chapter 61, pp. 358-363, (2015).
Sridhar et al., Anterior chamber tap: diagnostic and therapeutic indications in the management of ocular infections. Cornea. Oct. 2002;21(7):718-22.
Trivedi et al., Safety profile of anterior chamber paracentesis performed at the slit lamp. Clin Exp Ophthalmol. Nov. 2011;39(8):725-8.
Van Der Lelij et al., Diagnostic anterior chamber paracentesis in uveitis: a safe procedure? Br J Ophthalmol. Nov. 1997;81(11):976-9.
Wertheim et al., The minim technique for diagnostic anterior chamber paracentesis. Eye (Lond). Jun. 2009;23 (6):1491.
Wilczynski et al., Comparison of internal anterior chamber diameter measured with ultrabiomicroscopy with white-to-white distance measured using digital photography in aphakic eyes. Eur J Ophthalmol. Jan.-Feb. 2010;20(1):76-82.
International Search Report and Written Opinion for Application No. PCT/US2018/023862, dated Jun. 6, 2018. 7 pages.

* cited by examiner

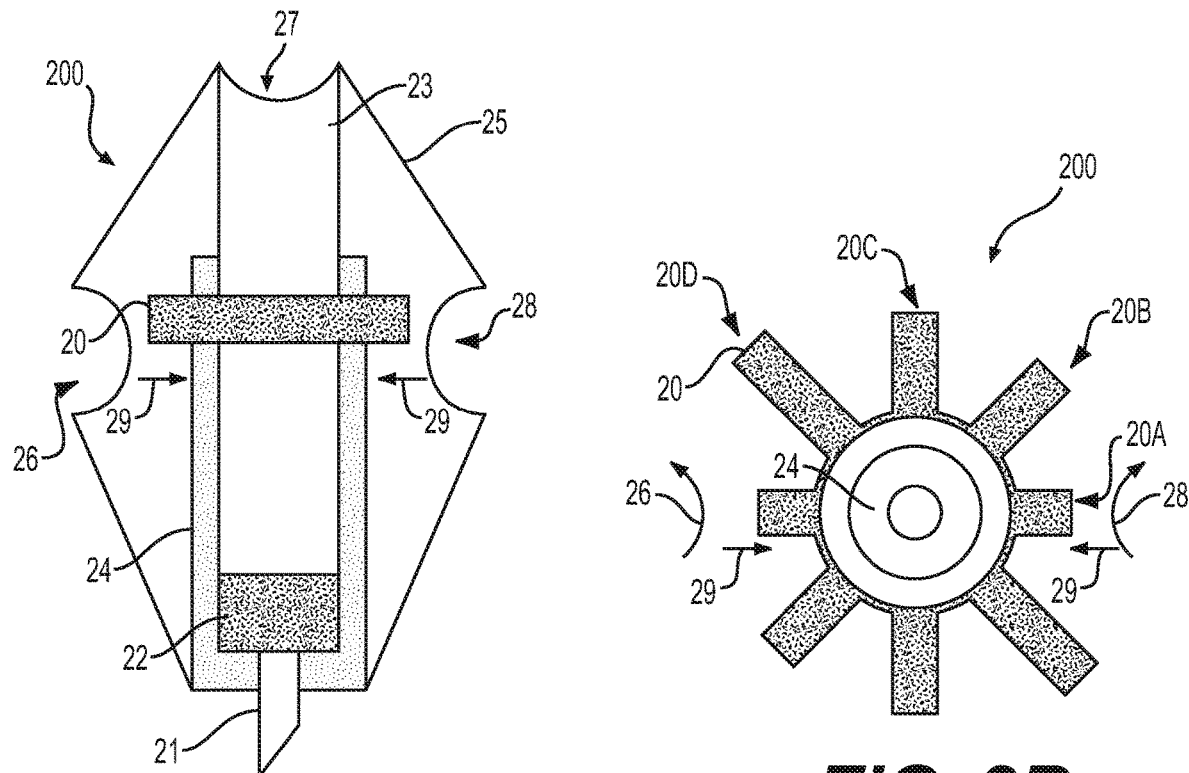
FIG. 2A
FIG. 2B
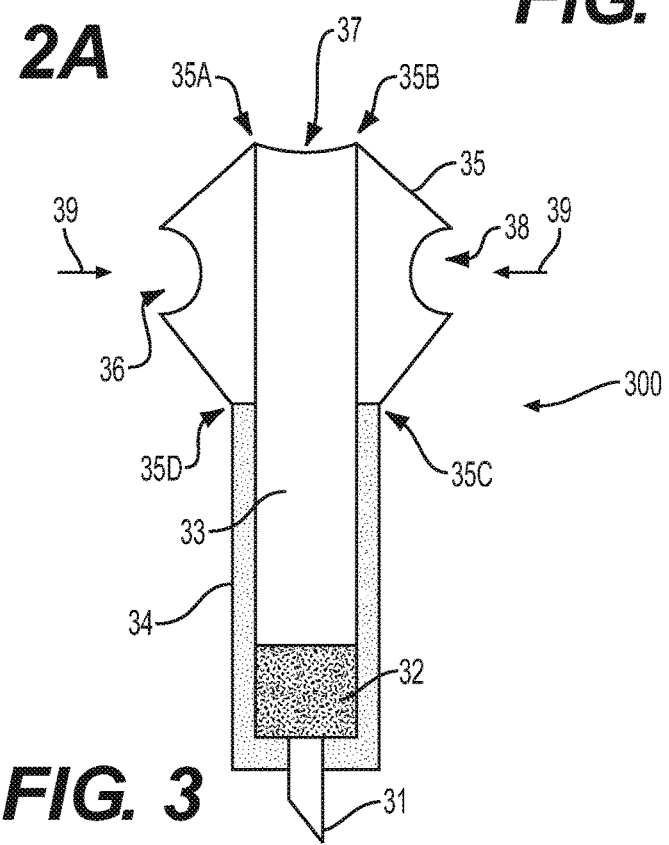
FIG. 3

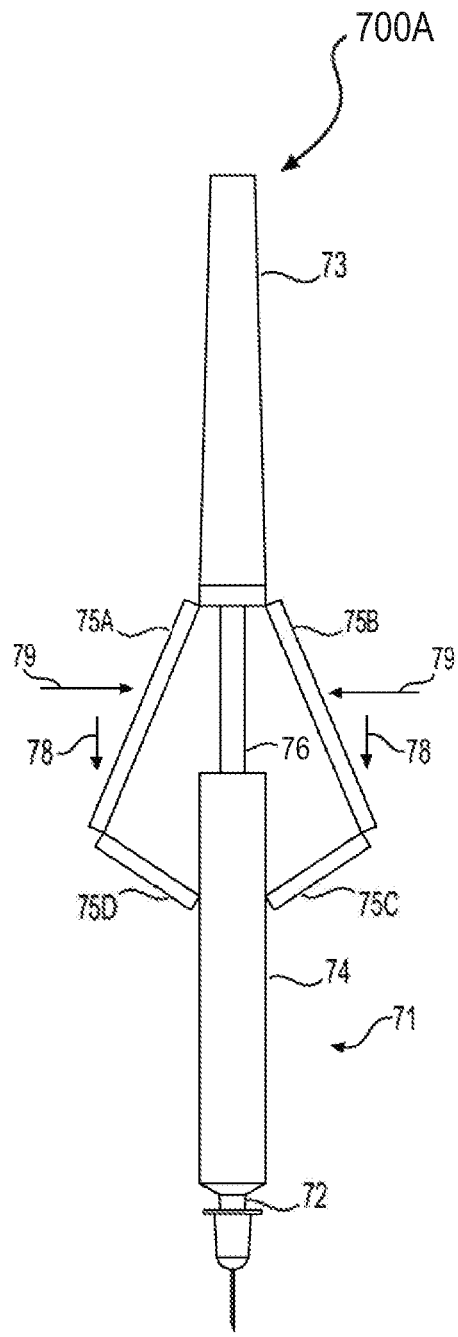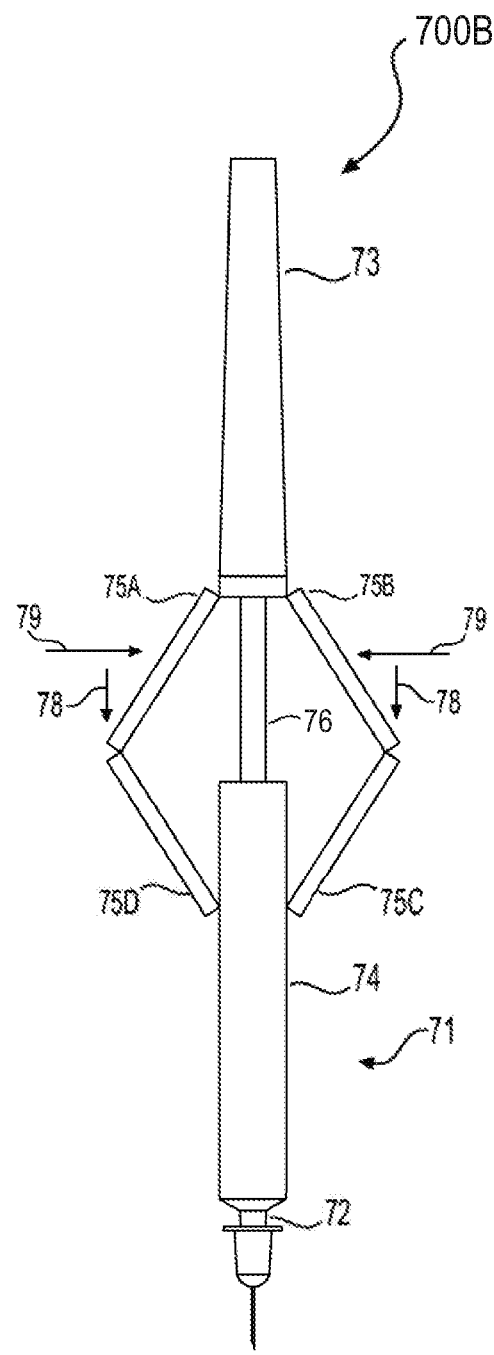
FIG. 7A    FIG. 7B

SYRINGE

RELATED APPLICATIONS

This application claims priority under 35 U.S.C. § 119 to U.S. Provisional Application No. 62/475,048, filed Mar. 22, 2017, the disclosure of which is herein incorporated by reference in its entirety.

TECHNICAL FIELD

The invention relates generally to an apparatus used in the field of medicine and more particularly to an apparatus used to aspirate or inject fluid from or into the body.

BACKGROUND

The eye is a fluid-filled, closed system with a one-way valve. The anterior chamber is the fluid-filled space inside the eye between the iris and the cornea's innermost surface, the endothelium. A normal anterior chamber depth is approximately between 2.5 mm and 3.5 mm and it contains approximately 0.25 mL of fluid called aqueous humor. Aqueous humor is produced by the ciliary body and flows from the posterior chamber to the anterior chamber. Once in the anterior chamber, the aqueous humor then travels through a fine trabecular meshwork at the anterior chamber angle (the one-way valve) and leaves via the Canal of Schlemm.

Intraocular pressure often measures between 10 and 22 mmHg. This pressure represents the balance between the production and outflow of aqueous humor. In some cases, intraocular pressure becomes elevated and may threaten visual loss. To treat such cases, fluid may be aspirated from the anterior chamber to lower the volume of the intraocular fluid, and consequently, lower the intraocular pressure. Anterior chamber paracentesis is the clinical term for removal of fluid from the anterior chamber of the eye, wherein intraocular pressure can reach dangerous levels.

There are numerous causes for the intraocular pressure to rise requiring urgent paracentesis of the anterior chamber including, but not limited to, closure of the anterior chamber angle and accumulation of blood or inflammatory cells in the anterior chamber. In addition, the treatment of certain ophthalmologic pathologies requires intraocular injection of medication or certain gases. These injections may lead to acute elevations in pressure that increase the risk of permanent vision loss and require an emergent paracentesis.

Lowering intraocular pressure below its normal level may also be desirable in some disease states. For instance, central retinal artery occlusion results from an atherosclerotic embolic event; acutely reducing intraocular pressure to levels below normal with a paracentesis will increase retinal perfusion in an attempt to propagate the embolus distally and minimize the amount of visual loss.

There are numerous nonemergent indications for an ophthalmologist to perform an anterior chamber paracentesis. Diagnostically, an anterior chamber paracentesis can be used for aqueous humor sampling for a suspected infection, inflammation, to diagnose certain intraocular cancers such as lymphoma, and for intraocular drug level monitoring.

The anterior chamber paracentesis is often performed in an office setting. One conventional method for performing paracentesis includes the use of a tuberculin syringe. The cornea is anesthetized and the patient is positioned in the slit lamp. The plunger of a tuberculin syringe is slightly withdrawn to break the bead on the syringe. The tip of the needle is positioned at the corneal limbus, the needle is gently inserted through the cornea and angled anteriorly to reduce the risk of the tip of the needle injuring the ciliary body, iris, or lens as it enters the anterior chamber. The plunger is slowly withdrawn and the desired fluid aspirated from the anterior chamber. The needle is then withdrawn from the eye.

Unfortunately, anterior chamber paracentesis is associated with serious, albeit infrequent, complications; these include endophthalmitis, corneal abscess, and mechanical trauma to the ciliary body, iris and lens. As a result, anterior chamber paracentesis is used with reluctance.

The conventional tuberculin needle and syringe are not designed for paracentesis and contain elements that increase procedural risk. These undesirable design elements include the needle length and flexibility, needle tip sharpness and bevel angle, syringe plunger mechanics, and barrel length, diameter, grip and shape.

The anterior chamber measures approximately 13 mm in diameter and 3 mm in depth and contains delicate ocular structures such as the cornea, ciliary body, iris, and lens. Insertion of the conventional 8 mm-12.7 mm tuberculin needle into this relatively small compartment means that even the smallest unintended movements on the part of a surgeon's hand or patient's eye or head exposes these intraocular structures to potential trauma, including resultant bleeding, infection, and vision loss. In addition to its undesirable length, the conventional needle stiffness, needle tip sharpness, and bevel angle are not optimized to penetrate the peripheral cornea. As a result, the force and angle required to access the anterior chamber is suboptimal, prolonging the procedure and increasing the risk of uncontrolled insertion and patient movement.

A conventional tuberculin syringe contains a plunger that requires withdrawal in order to initiate and propagate suction. It is technically difficult for a surgeon to draw back the plunger while holding the syringe barrel steady with the needle inside the anterior chamber. Therefore, the surgeon may ask an assistant to withdraw the plunger while the surgeon attempts to hold the syringe and needle steady inside the eye. This cumbersome tandem procedure reduces the surgeon's control over needle depth and direction, increasing risk of intraocular trauma, and reduces the surgeon's control over withdrawal volume. Alternatively, the surgeon removes the plunger before the procedure, in which case aqueous fluid spontaneously leaks into the empty barrel in an uncontrolled fashion, further compromising the precision with which the desired volume of aqueous fluid is removed and creating a dangerous portal exposing the intraocular compartment to infectious external contamination.

The anterior chamber contains approximately 0.25 mL of aqueous fluid. A conventional tuberculin syringe barrel holds 1 mL volume, with gradations marked for every 0.01 mL. Therefore, the precision with which a surgeon can measure a desired volume of aqueous is limited to an approximation. In addition, the barrel's smooth surface, round shape and thin diameter are suboptimal for the fine motor manipulation and hand control required to perform a paracentesis. As a result of the above undesirable syringe features, the conventional paracentesis procedure may be unreliable, unpredictable, inconsistent and dangerous.

In contrast to a paracentesis, an intracameral injection is the injection of fluid into the anterior chamber. This procedure may be indicated to increase intraocular pressure if the pressure is too low, to inject medications such as anti-infective agents, and for other medical reasons. Similar to the paracentesis, surgeons use conventional syringes to perform intracameral injections, thereby exposing the intraocular tissues to an unnecessary risk of trauma.

The paracentesis and injection devices and methods of the present disclosure are advantageous for use in medicine and particularly in the field of ophthalmology. That is, paracentesis and injection devices taught herein enable a practitioner to withdraw or inject fluid from, and into a person or animal using one hand, with or without the visual guide of a slit lamp or other radiologic or ultrasound guiding devices.

SUMMARY

The embodiments of the present disclosure contain a needle designed to allow a practitioner to aspirate or inject without contacting surrounding structures. The above characteristics of the devices taught herein can be particularly advantageous when trying to withdraw or inject fluid in or around an organ with delicate surrounding structures that are vulnerable to inadvertent trauma, such as the human eye.

The embodiments of the present disclosure allow a practitioner to aspirate or inject a precise, controllable volume of fluid. This can be particularly advantageous when withdrawing fluid from a closed chamber that is vulnerable to internal pressure variations, or when injecting medication with a narrow therapeutic index.

The embodiments of the present disclosure differ from conventional instruments in that, during use, the length of the needle is designed to penetrate the anterior chamber of the eye only far enough as to aspirate or inject a desired fluid and not to reach other intraocular structures such as the iris, ciliary body, or lens. Additionally, the stiffness, sharpness, and bevel angle of the needle of the presently disclosed device are designed for penetrating the cornea.

Additionally, a differentiating feature of the syringe of the present disclosure is the ability to operate the device with only one hand. A second user, such as a nurse or assistant is not needed to manipulate the syringe plunger, as is often required with the conventional devices and methods. Further still, the syringe of the present disclosure does not require special visualization equipment to aspirate or inject a specified amount of fluid.

The embodiments of the present disclosure provide the practitioner with flexibility in selecting a preferred insertion site to access the anterior chamber of the eye. With a conventional device in an ophthalmology application, the needle must be inserted horizontally along the iris plane at the corneal limbus. In the devices taught herein, the needle can be inserted horizontally along the iris plane at the corneal limbus, and can also be inserted safely at any point between the anterior edge of the surgical limbus and the visual axis perpendicular to the corneal curvature. This can be particularly advantageous by making the insertion less awkward or cumbersome, if the patient's eye or head is not steady, or if the limbus is scarred or otherwise difficult to access.

The embodiments of the present disclosure allow a practitioner to perform the paracentesis with enhanced sterility over other methods of paracentesis, since it is a closed system. In existing paracentesis methods, a surgeon will remove the plunger before the procedure, creating a dangerous portal exposing the intraocular compartment to outside infectious contamination.

It will be obvious to anyone practicing medicine outside the field of ophthalmology that the devices taught herein can be used, or modified to withdraw, collect or inject fluid from or into other parts of the body. For instance, lumbar puncture (spinal tap) is performed in the lower back, in the lumbar region. During lumbar puncture, a needle is inserted between two lumbar bones (vertebrae) to remove a sample of cerebrospinal fluid—the fluid that surrounds the brain and spinal cord to protect them from injury.

A lumbar puncture can help diagnose serious infections, such as meningitis; other disorders of the central nervous system, such as Guillain-Barre syndrome and multiple sclerosis, or cancers of the brain or spinal cord. Sometimes doctors use lumbar puncture to inject anesthetic medications or chemotherapy drugs into the cerebrospinal fluid. Other times it is used to measure or relieve the cerebrospinal fluid pressure.

Injections performed in areas other than the eye may require precise manual control in order to access a particular tissue. For instance, intradermal injections are used for sensitivity tests, such as tuberculosis, allergy, and local anesthesia tests, as well as for vaccinations. Conventional syringes require multiple hand maneuvers that can lead to increased risk of injecting fluid into an undesirable location, such as the subcutaneous, or muscle layer, beneath the skin.

In some embodiments of the present disclosure, an aspiration and/or injection device for use in the field of medicine, and more specifically for use in ophthalmology to aspirate or inject fluids from or into the anterior chamber, is provided. The device advantageously provides a safe, simple, inexpensive aspirating or injecting syringe and includes a barrel (for collection of aspirated fluids, or for injection) a plunger and plunger seal, a needle to access the anterior chamber, and a handle which when squeezed directs the plunger rearwardly away from the injection site to aspirate the fluid into the barrel or toward the injection site to inject from the barrel.

In some embodiments, a syringe is provided comprising a syringe barrel having a first end couplable to a needle and an open second end. Additionally, the syringe of the present invention comprises a plunger seal disposed inside the syringe barrel and a plunger rod in the syringe barrel extending along a longitudinal axis between a first end coupled to the plunger seal and a second end opposite of the first end. The syringe further comprises a compressible handle coupled between a portion of the syringe barrel and the second end of the plunger rod, wherein compressing the compressible handle causes the syringe plunger to move rearwardly in the syringe barrel away from the needle.

In some embodiments of the present disclosure, a syringe is provided, comprising a syringe barrel having a first end couplable to a needle and an open second end and a plunger seal disposed inside the syringe barrel. The syringe further comprises a plunger rod disposed in the syringe barrel extending along a longitudinal axis between a first end coupled to the plunger seal and a second end opposite of the first end. The syringe comprises a compressible handle coupled between a portion of the syringe barrel and the second end of the plunger rod, wherein compressing the compressible handle causes the syringe plunger to move forwardly in the syringe barrel toward the needle.

In some embodiments of the present disclosure, a method for aspirating a fluid is provided comprising inserting a needle of a syringe device into a chamber such that the needle is in fluid communication with both an interior of the chamber and a syringe barrel of the syringe. The syringe comprises a plunger seal disposed inside the syringe barrel, and a plunger rod disposed in the syringe barrel extending along a longitudinal axis between a first end coupled to the plunger seal and a second end opposite of the first end. The syringe further comprises a compressible handle coupled between a portion of the syringe barrel and the second end of the plunger rod. The method for aspirating a fluid also comprises compressing the compressible handle to move the plunger rod and the plunger seal rearwardly within the syringe barrel away from the needle to draw fluid from the chamber into the syringe barrel.

In some embodiments, a method for injecting a fluid is provided comprising inserting a needle of a syringe device into an injection site. The syringe includes a plunger seal disposed inside a syringe barrel, and a plunger rod disposed in the syringe barrel extending along a longitudinal axis between a first end coupled to the plunger seal and a second end opposite of the first end. The syringe further comprises a compressible handle coupled between a portion of the syringe barrel and the second end of the plunger rod. The method for injecting a fluid further comprises compressing the compressible handle to move the plunger rod and the plunger seal forwardly within the syringe barrel toward the needle to inject a fluid from the syringe barrel into the injection site.

Still other objects and advantages of the invention will in part be obvious and will in part be apparent from the specification and drawings.

BRIEF DESCRIPTION OF THE DRAWINGS

The accompanying figures illustrate one or more embodiments of the invention. The drawings are not necessarily to scale. The present invention is illustrated by way of example, and not limitation, in the accompanying figures wherein:

FIG. 2A illustrates a plan view of an embodiment of a syringe including a stopper, according to various embodiments of the present disclosure.

FIG. 2B illustrates a cross-sectional view of the syringe of FIG. 2A from a horizontal plane extending through a stopper, according to various embodiments of the present disclosure.

FIG. 3 illustrates a plan view of another embodiment of a syringe, according to various embodiments of the present disclosure.

FIGS. 7A-7F illustrate a plan view of other embodiments of a syringe with varying handle and plunger lengths, according to various embodiments of the present disclosure.

DETAILED DESCRIPTION

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints. "Multiple" will be understood to refer to two or more.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Figure 1A:
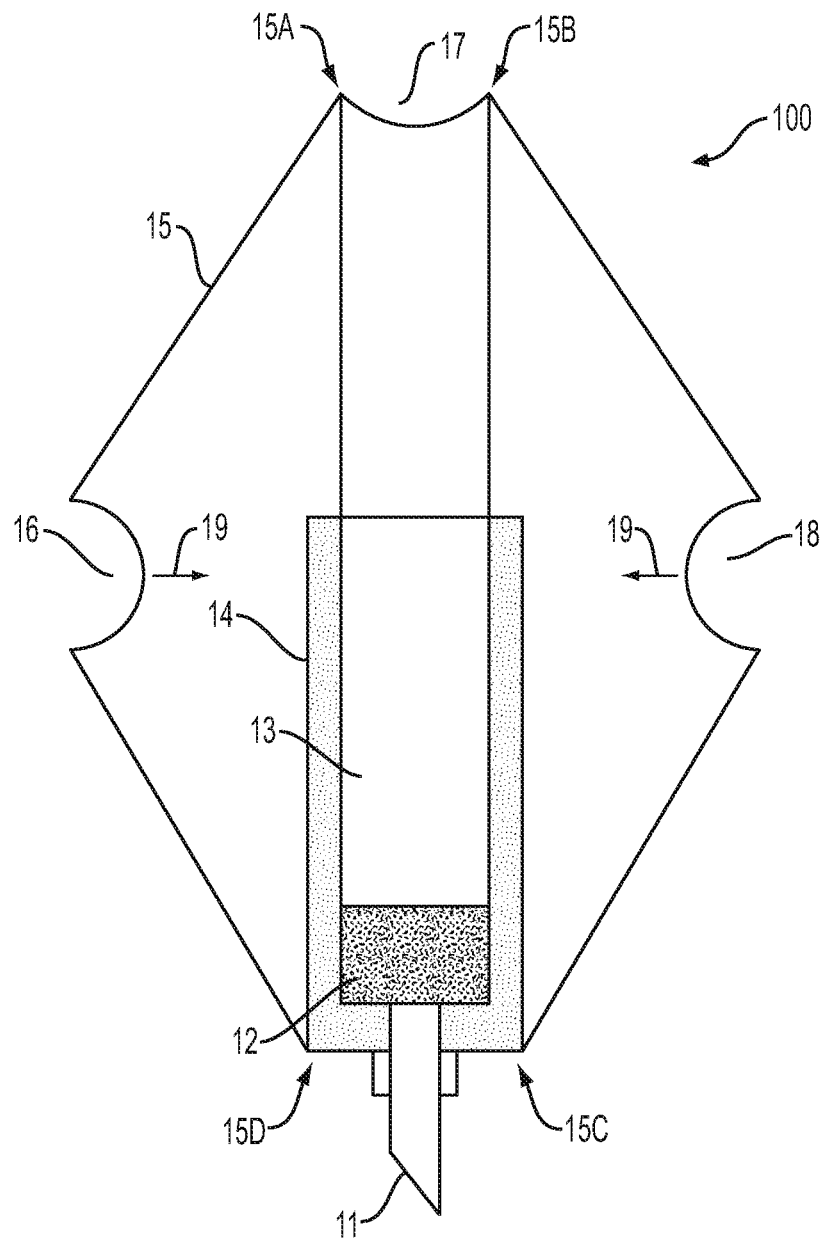
FIG. 1A illustrates a cross-sectional view of a syringe, according to various embodiments of the present disclosure.

Referring first to FIG. 1A, a cross-sectional view of a syringe 100 in accordance with an embodiment of the present disclosure is illustrated. As is depicted, the syringe 100 includes a needle 11 attached to a barrel 14, and a plunger 13 and a plunger seal 12 disposed, at least in part, within the barrel 14. The handle 15 is attached to, or near, the plunger 13 at, or near, terminal endpoints 15A, 15B, and to, or near, the barrel 14 at, or near, terminal endpoints 15D, 15C.

In various embodiments, the handle 15 is provided in two or more components disposed on different regions of the outer surface of the barrel 14 and the plunger 13. In some embodiments, the components of the handle 15 are disposed in diametrical opposition about the barrel 14 and the plunger 13. The handle 15 may be configured to manipulate the plunger 13, while remaining sufficiently flexible to be compressed in the direction of the arrows 19. The handle 15 may be provided in a variety of materials, including, but not limited to, various metals, composite materials, and plastics, such as polyethylene, polypropylene, or polyvinyl chloride.

The handle 15 can connect to the plunger 13 and the barrel 14 in a variety of ways. For example, the terminal endpoints 15A, 15B, 15D, 15C may comprise connectors that facilitate compression of the handle 15. For example, the terminal endpoints 15A, 15B, 15D, 15C may comprise living hinges, pin joints, spring hinges, or the like. Alternatively, the handle 15 can be connected to the plunger 13 and the barrel 14 using a variety of chemical means, including various adhesives, epoxies, welding, or the like. Additionally, in various embodiments, the handle 15, the plunger 13, and the barrel 14 may comprise a single, injection-molded component.

In various embodiments, the handle 15 includes grips 16, 18 which provide a resting surface for the fingers of the operator of the syringe 100. In some embodiments, the grips 16, 18 are diametrically disposed about the barrel 14, and are provided in a variety of shapes and sizes. For example, the grips 16, 18 may be provided as concave, semi-circular recesses in the outer surface of the handle 15. In other embodiments, for example, the grips 16, 18 can be provided in similar sizes and shapes, or can be provided in differing sizes and shapes to accommodate various possible geometries of an operator's fingers. Additionally, for example, the grips 16, 18 can include ergonomic contours or silicone pads to reduce pressure points and improve comfort of the syringe 100 during use.

In some embodiments, the syringe 100 includes a grip 17 disposed on, or proximate to the plunger 13. The grip 17 provides another resting surface of at least one finger of an operator, and enables enhanced manipulation of the device. For example, an operator may place an index finger on the grip 17, a thumb on the grip 18, and a middle finger on the grip 16. An operator may rest their remaining fingers on various other components or surfaces of the device, including on the handle 15 or the barrel 14.

The syringe 100 comprises a needle 11 with a gauge, stiffness, bevel and length to facilitate penetration of the outer layer of the eye, namely the cornea, just slightly entering the anterior chamber, minimizing the risk of contacting other intraocular structures. In various embodiments, the length of needle 11 is configured to slightly enter the anterior chamber during use of the syringe 100. The length of the needle 11 can be about, more than, or less than 0.25, 0.50, 0.75, 1.0, 1.25, 1.50, 1.75, 2.0, 2.25, 2.50, 2.75, 3.0, 3.25, 3.50, 3.75, 4.0, 4.25, 4.50, 4.75 or 5.0 mm. These values can be used to define discrete lengths, such as 0.75 or 3.0 mm. These values can also be used to define a range of lengths, such as from about 0.50 to about 1.0 mm, or from about 2.75 to about 3.0 mm.

Additionally, in various embodiments, the gauge of the needle 11 may be configured to facilitate penetration of the outer layer of the eye, namely the cornea. The gauge of the needle 11 can be about, more than, or less than 19, 20, 21, 22, 23, 24, 25, 26, 27, 28, 29, 30, 31, 32, 33, or 34 g. These values can be used to define discrete gauges, such as 25 g or 27 g. These values can also be used to define a range of gauges, such as from about 26 to 28 g, or from about 25 to 32 g.

Additionally, in various embodiments, the needle 11 may be coated with various materials, such as silicone, to facilitate penetration through the cornea, or hydrophilic coatings to reduce friction between biologic tissues and the needle 11. Further, the needle 11 may include various tip configurations to facilitate penetration of bodily tissue, such as ocular tissue. For example, in various embodiments, the needle 11 may comprise a beveled tip, provided in a variety of bevel angles.

In some embodiments, during use of the syringe 100, pressure is placed on the grip 17, and the grips 16, 18 are grasped to stabilize the device while the operator advances the needle 11 into the anterior chamber of the eye. Once the needle 11 has penetrated the outer layer of the eye (i.e. the cornea), and its tip is within the anterior chamber, pressure is applied on the grips 16 and 18 in the direction of the arrows 19 (i.e. the handle 15 is compressed). As a result, since the plunger 13 and the plunger seal 12 are attached to one another and can move freely within the barrel 14, the action of moving the grips 16, 18 in the direction of the arrows 19 causes the handle 15 to straighten, withdrawing the plunger 13 and the plunger seal 12 rearwardly, away from the needle 11. In turn, the plunger 13 extends further out of the barrel 14, and the plunger seal 12 moves closer to the open end of the barrel 14, generating negative pressure in the barrel 14 to draw out fluid from the anterior chamber of the eye into the barrel 14.

Figure 1B:
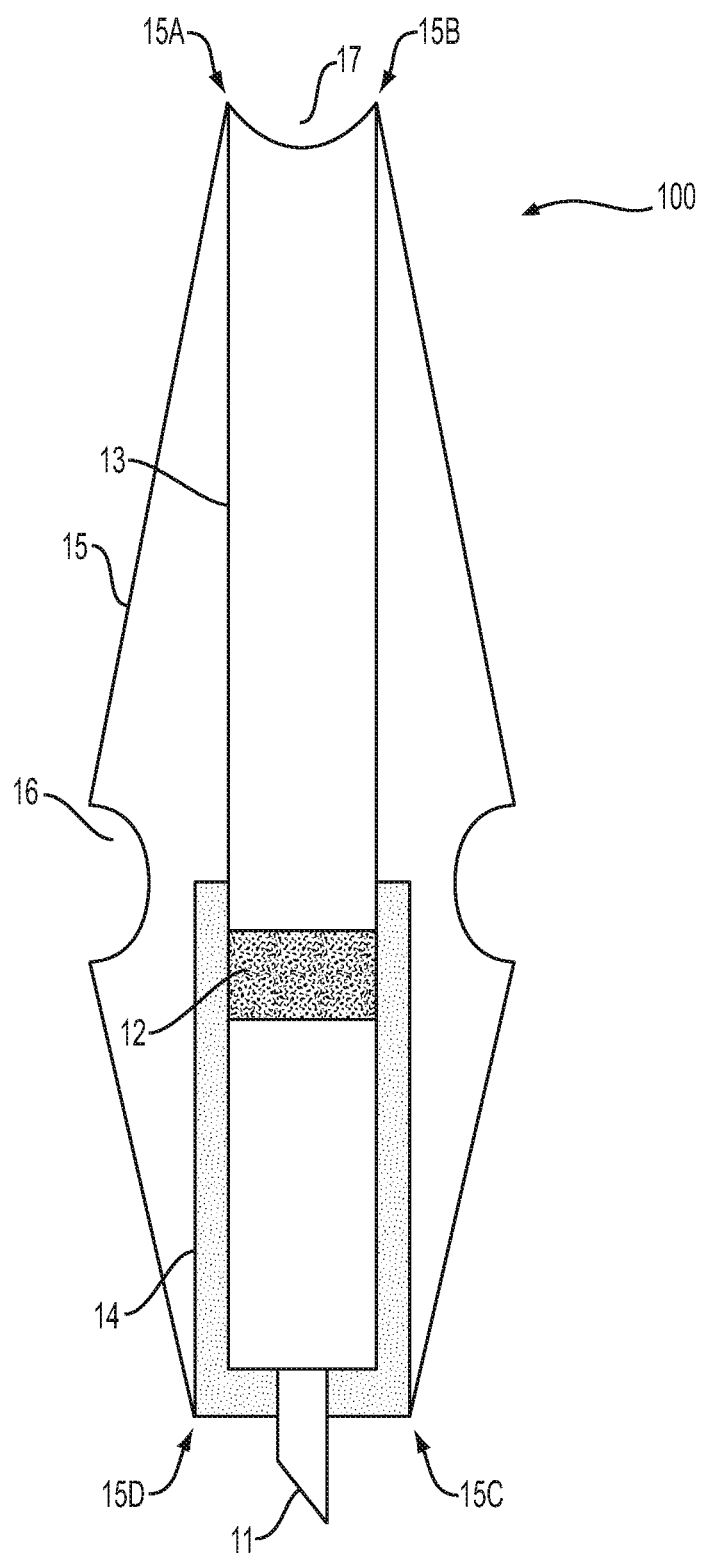
FIG. 1B illustrates a cross-sectional view of the syringe from FIG. 1A, showing the syringe after the syringe handles have been squeezed to retract the plunger.

FIG. 1B illustrates a cross-sectional view of the syringe 100 from FIG. 1A, showing the syringe 100 after the handles 15 have been compressed by applying pressure to the grips 16, 18 in the direction of the arrows 19. This motion causes the handle 15 to straighten, moving the grips 16, 18 closer to each other (i.e. compressing the handle 15), and withdrawing the plunger 13 and the plunger seal 12 rearwardly away from the needle 11. In turn, the plunger 13 extends further out of the barrel 14, and the plunger seal 12 moves closer to the open end of the barrel 14, generating negative pressure in the barrel 14 to draw fluid into the barrel 14.

In various embodiments, the syringe 100 can be configured such that the maximum distance that the grips 16 and 18 can travel corresponds to a certain volume of withdrawn fluid. In some embodiments, the grips 16, 18 are prevented from compressing further by contact with the outer surface of the barrel 14. In other embodiments, some other mechanical limiter can limit the movement of the grips 16, 18, such as a physical stop or some upper threshold of device design and/or flexibility of the material of the handle 15. This safe stop feature of the syringe 100 allows an operator to use the syringe 100 without an assistant or direct visualization of the withdrawn liquid.

In some embodiments, the maximum volume of withdrawn fluid is adjusted by changing the angle of the handle 15 relative to the barrel 14. For example, increasing the angle of the handle 15 relative to the barrel 14 increases the distance between the grips 16, 18, which allows the plunger 13 to be retracted further within the barrel 14, thereby increasing the volume of fluid able to be withdrawn using the syringe 100. Conversely, a smaller angle of the handle 15 relative to the barrel 14 results in a shorter distance between the grips 16, 18, limiting the distance the plunger 13 can be retracted within the barrel 14, thereby decreasing the volume of fluid able to be withdrawn using the syringe 100.

FIG. 2A illustrates a plan view of an embodiment of a syringe 200 including a stopper 20, according to various embodiments of the present disclosure. As is depicted, the syringe 200 includes a needle 21 attached to a barrel 24, and a plunger 23 and a plunger seal 22 disposed, at least in part, within the barrel 24. The handle 25 is attached to, or near, the plunger 23 at, or near, a first end, and to, or near, the barrel 24 at, or near, a second end.

In various embodiments, the handle 25 is provided in two or more components disposed on different regions of the outer surface of the barrel 24 and the plunger 23. In some embodiments, the components of handle 25 are disposed in diametrical opposition about the barrel 24 and the plunger 23. The handle 25 may be configured to manipulate the plunger 23, while remaining sufficiently flexible to be compressed in the direction of the arrows 29. The handle 25 may be provided in a variety of materials, including, but not limited to, various metals, composite materials, and plastics, such as polyethylene, polypropylene, or polyvinyl chloride.

The handle 25 can connect to the plunger 23 and the barrel 24 in a variety of ways. For example, the handle 25 may comprise connectors that facilitate compression of the handle 15. For example, the handle 25 may be connected to the plunger 23 and the barrel 24 with living hinges, pin joints, spring hinges, or the like. Alternatively, the handle 25 can be connected to the plunger 23 and the barrel 24 using a variety of chemical means, including various adhesives, epoxies, welding, or the like. Additionally, in various embodiments, the handle 25, the plunger 23, and the barrel 24 may be provided as a single, injection-molded component.

In various embodiments, the handle 25 includes grips 26, 28 which provide a resting surface for the fingers of the operator of the syringe 200. In some embodiments, the grips 26, 28 are diametrically disposed about the barrel 24, and are provided in a variety of shapes and sizes. For example, the grips 26, 28 may be provided as concave, semi-circular recesses in the outer surface of the handle 25. In other embodiments, for example, the grips 26, 28 can be the provided in similar sizes and shapes, or can be provided in differing sizes and shapes to accommodate various possible geometries of an operator's fingers. Additionally, for example, the grips 26, 28 can include ergonomic contours or silicone pads to reduce pressure points and improve comfort of the syringe 200 during use.

In some embodiments, the syringe 200 includes a grip 27 disposed on, or proximate to the plunger 23. The grip 27 provides another resting surface of at least one finger of an operator, and enables enhanced manipulation of the device. For example, an operator may place an index finger on the grip 27, a thumb on the grip 28, and a middle finger on the grip 26. An operator may rest their remaining fingers on various other components or surfaces of the device, including on the handle 25 or the barrel 24.

In various embodiments, the syringe 200 comprises a needle 21 with a gauge, stiffness, bevel, and length to facilitate penetration of bodily tissue, such as the outer layer of the eye, namely the cornea, just slightly entering the anterior chamber, minimizing the risk of contacting other intraocular structures.

In some embodiments, the maximum volume of withdrawn fluid is adjusted by changing the angle of the handle 25 relative to the barrel 24. For example, increasing the angle of the handle 25 relative to the barrel 24 increases the distance between the grips 26, 28, which allows the plunger 23 to be retracted further within the barrel 24, thereby increasing the volume of fluid able to be withdrawn using syringe 200. Conversely, a smaller angle of the handle 25 relative to the barrel 24 results in a shorter distance between the grips 26, 28, limiting the distance the plunger 23 can be retracted within the barrel 24, thereby decreasing the volume of fluid able to be withdrawn using the syringe 200.

In various embodiments, the syringe 200 includes a stopper 20, which provides a fixed stopping distance for grips 26, 28. For example, when grips 26, 28 are squeezed together in the direction of the arrows 29, after they travel a set distance, their movement is stopped by stopper 20. In various embodiments, stopper 20 is adjustable. For example, stopper 20 can be configured such that adjusting or rotating stopper 20 changes its outer width, thus changing the distance that the grips 26, 28 can move during use. This functionality enables adjustment of the volume of the fluid that can be extracted during use, such as during a paracentesis procedure, (e.g. by applying pressure to the grips 26, 28 until the they are stopped by the stopper 20). The stopper 20 eliminates the need for direct visualization of the barrel 24 during use, which is often necessary with conventional devices to determine the volume of extracted fluid. This also frees users to focus on keeping the syringe 200 steady while it is within and proximate sensitive tissue.

In some embodiments, during use of the syringe 200, pressure is placed on the grip 27, and the grips 26, 28 are grasped to stabilize the syringe 200 while the operator advances the needle 21 into a region of the body, for example, the anterior chamber of the eye. Once the needle 21 has penetrated the outer layer of the eye (i.e. the cornea), and its tip is within the anterior chamber, pressure is applied to the grips 26 and 28 in the direction of the arrows 29 (i.e. the handle 25 is compressed). As a result, since the plunger 23 and the plunger seal 22 are attached to one another and can move freely within the barrel 24, the action of moving the grips 26, 28 in the direction of the arrows 29 causes the handle 25 to straighten, withdrawing the plunger 23 and the plunger seal 22 rearwardly, away from the needle 21. In turn, the plunger 23 extends further out of the barrel 24, and the plunger seal 22 moves closer to the open end of the barrel 24, generating negative pressure in the barrel 24 to draw out fluid from the anterior chamber of the eye into the barrel 24.

FIG. 2B illustrates a cross-sectional view of the syringe 200 of FIG. 2A from a horizontal plane extending through the stopper 20, according to various embodiments of the present disclosure. In various embodiments, the stopper 20 is a circular dial that surrounds the barrel 24. In some embodiments, the maximum distance the grips 26, 28 can travel can be adjusted by rotating the stopper 20 about the barrel 24. In various embodiments, the stopper 20 can be rotated to result in multiple options for a maximum travelling distance for the grips 26, 28. For example, the stopper 20 can be rotated to achieve desired elevations 20A, 20B, 20C, 20D. Each elevation 20A, 20B, 20C, 20D provides a distinct geometry which determines the distance that the grips 26, 28 can travel when squeezed in the direction of the arrows 29. As a result, the elevation of the stopper 20 can determine how far the plunger 23, and the plunger seal 22 retract in barrel 24, away from the needle 21. This, in turn, determines the volume of fluid extracted during use of syringe 200.

As is depicted in FIG. 2B, the stopper 20 at elevation 20A extends the shortest distance from the barrel 24, enabling the grips 26, 28 to move the greatest distance in the direction of the arrows 29, and thus, providing a large allowable fluid extraction volume. The stopper 20 at elevation 20B extends a further distance from the barrel 24, limiting the traveling distance of the grips 26, 28 in the direction of the arrows 29 during the procedure. The stopper 20 at elevation 20C extends even further from the barrel 24, limiting the available travelling distance of the grips 26, 28 to a greater degree. The stopper 20 at elevation 20D extends the furthest distance from the barrel 24, providing the most limited travelling distance of the grips 26, 28, and thus, the smallest fluid extraction volume. Various elevations can be provided in embodiments of the present disclosure, corresponding to various allowable extraction volumes. As stated above, the stopper 20 is beneficial during use of the syringe 200, such as during a paracentesis procedure, to eliminate user variability and to maximize control of the device, without distracting the user during the procedure.

FIG. 3 illustrates a plan view of an embodiment of a syringe 300, according to various embodiments of the present disclosure. The syringe 300 includes a needle 31 attached to a barrel 34, and a plunger 33 and a plunger seal 32 disposed, at least in part, within the barrel 34. The handle 35 is attached to, or near, the plunger 33 at, or near, terminal endpoints 35A, 35B, and to, or near, the barrel 34 at, or near, terminal endpoints 35D, 35C. In the syringe 300, the terminal endpoints 35D, 35C are disposed at, or near, the open end of the barrel 34. In various embodiments, attaching the handle 35 at, or near, the open end of the barrel 34 results in a handle 35 of a smaller size, which may be more aptly suited for users with smaller hands, or for procedures extracting only small volumes of fluid.

In various embodiments, the handle 35 is provided in two or more components disposed on different regions of the outer surface of the barrel 34 and the plunger 33. In some embodiments, the components of the handle 35 are disposed in diametrical opposition about the barrel 34 and the plunger 33. The handle 35 may be configured to manipulate the plunger 33, while remaining sufficiently flexible to be compressed in the direction of the arrows 39. The handle 35 may be provided in a variety of materials, including, but not limited to, various metals, composite materials, and plastics, such as polyethylene, polypropylene, or polyvinyl chloride.

The handle 35 can connect to the plunger 33 and the barrel 34 in a variety of ways. For example, the terminal endpoints 35A, 35B, 35D, 35C may comprise connectors that facilitate compression of the handle 35. For example, the terminal endpoints 35A, 35B, 35D, 35C may comprise living hinges, pin joints, spring hinges, or the like. Alternatively, the handle 35 can be connected to the plunger 33 and the barrel 34 using a variety of chemical means, including various adhesives, epoxies, welding, or the like. Additionally, in various embodiments, the handle 35, the plunger 33, and the barrel 34 may comprise a single, injection-molded component.

In various embodiments, the handle 35 includes grips 36, 38 which provide a resting surface for the fingers of the operator of the syringe 300. In some embodiments, the grips 36, 38 are diametrically disposed about the barrel 34, and are provided in a variety of shapes and sizes. For example, the grips 36, 38 may be provided as concave, semi-circular recesses in the outer surface of the handle 35. In other embodiments, for example, the grips 36, 38 can be provided in similar sizes and shapes, or can be provided in differing sizes and shapes to accommodate various possible geometries of an operator's fingers. Additionally, for example, the grips 36, 38 can include ergonomic contours or silicone pads to reduce pressure points and improve comfort of the syringe 300 during use.

In some embodiments, the syringe 300 includes a grip 37 disposed on, or proximate to the plunger 33. The grip 37 provides another resting surface of at least one finger of an operator, and enables enhanced manipulation of the device. For example, an operator may place an index finger on the grip 37, a thumb on the grip 38, and a middle finger on the grip 36. An operator may rest their remaining fingers on various other components or surfaces of the device, including on the handle 35 or the barrel 34.

The syringe 300 comprises a needle 31 with a gauge, stiffness, bevel and length to facilitate penetration of the outer layer of the eye, namely the cornea, just slightly entering the anterior chamber, minimizing the risk of contacting other intraocular structures.

In some embodiments, during use of the syringe 300, pressure is placed on the grip 37, and the grips 36, 38 are grasped to stabilize the device while the operator advances the needle 31 into the anterior chamber of the eye. Once the needle 31 has penetrated the outer layer of the eye (i.e. the cornea), and its tip is within the anterior chamber, pressure is applied on the grips 36 and 38 in the direction of the arrows 39 (i.e. the handle 35 is compressed). As a result, since the plunger 33 and the plunger seal 32 are attached to one another and can move freely within the barrel 34, the action of moving the grips 36, 38 in the direction of the arrows 39 causes the handle 35 to straighten, withdrawing the plunger 33 and the plunger seal 32 rearwardly, away from the needle 31. In turn, the plunger 33 extends further out of the barrel 34, and the plunger seal 32 moves closer to the open end of the barrel 34, generating negative pressure in the barrel 34 to draw out fluid from the anterior chamber of the eye into the barrel 34.

In various embodiments, the syringe 300 can be configured such that the maximum distance that the grips 36 and 38 can travel corresponds to a certain volume of withdrawn fluid. In some embodiments, contact with the outer surface of the barrel 34 prevents the grips 36, 38 from compressing further. In other embodiments, some other mechanical limiter can limit the movement of the grips 36, 38, such as stopper 20. This safe stop feature of the syringe 300 allows an operator to use the syringe 300 without an assistant or direct visualization of the withdrawn liquid.

Figure 4:
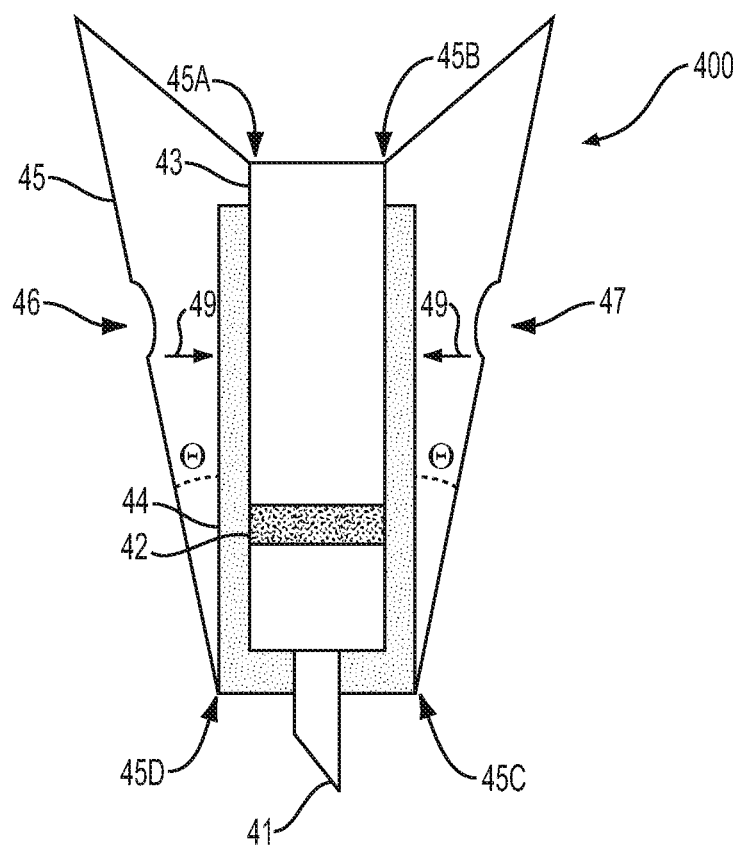
FIG. 4 illustrates a plan view of another embodiment of a syringe having varying arm lengths, according to various embodiments of the present disclosure.

In some embodiments, the maximum volume of withdrawn fluid is adjusted by changing the angle of the handle 35 relative to the barrel 34. For example, increasing the angle of the handle 35 relative to the barrel 34 increases the distance between the grips 36, 38, which allows the plunger 33 to be retracted further within the barrel 34, thereby increasing the volume of fluid able to be withdrawn using syringe 300. Conversely, a smaller angle of the handle 35 relative to the barrel 34 results in a shorter distance between the grips 36, 38, limiting the distance the plunger 33 can be retracted within the barrel 34, thereby decreasing the volume of fluid able to be withdrawn using the disclosed device FIG. 4 illustrates a plan view of another embodiment of a syringe 400 including handles with different lengths, according to various embodiments of the present disclosure. In various embodiments, the syringe 400 includes a needle 41 attached to a barrel 44, and a plunger 43 and a plunger seal 42 disposed, at least in part, within the barrel 44. The handle 45 is attached to, or near, the plunger 43 at, or near, terminal endpoints 45A, 45B, and to, or near, the barrel 44 at, or near, terminal endpoints 45D, 45C.

In various embodiments, the handle 45 is provided in two or more components disposed on different regions of the outer surface of the barrel 44 and the plunger 43. In some embodiments, the components of the handle 45 are disposed in diametrical opposition about the barrel 44 and the plunger 43. The handle 45 may be configured to manipulate the plunger 43, while remaining sufficiently flexible to be compressed in the direction of the arrows 49. The handle 45 may be provided in a variety of materials, including, but not limited to, various metals, composite materials, and plastics, such as polyethylene, polypropylene, or polyvinyl chloride.

In various embodiments, the components of the handle 45 each comprise a first arm of a first length and a second arm of a second length, wherein the first length is shorter than the second length. In some embodiments, the first and second arms of the handle 45 are flexibly connected both to each other, to the barrel 44, and to the plunger 43.

The handle 45 can connect to the plunger 43 and the barrel 44 in a variety of ways. For example, the terminal endpoints 45A, 45B, 45D, 45C may comprise connectors that facilitate compression of the handle 45. For example, the terminal endpoints 45A, 45B, 45D, 45C may comprise living hinges, pin joints, spring hinges, or the like. Alternatively, the handle 45 can be connected to the plunger 43 and the barrel 44 using a variety of chemical means, including various adhesives, epoxies, welding, or the like. Additionally, in various embodiments, the handle 45, the plunger 43, and the barrel 44 may be provided as a single, injection-molded component.

In various embodiments, the handle 45 includes grips 46, 47 which provide a resting surface for the fingers of the operator of the syringe 400. In some embodiments, the grips 46, 47 are diametrically disposed about the barrel 44, and are provided in a variety of shapes and sizes. For example, the grips 46, 47 may be provided as concave, semi-circular recesses in the outer surface of the handle 45. In other embodiments, for example, the grips 46, 47 can be the provided in similar sizes and shapes, or can be provided in differing sizes and shapes to accommodate various possible geometries of an operator's fingers. Additionally, for example, the grips 46, 47 can include ergonomic contours or silicone pads to reduce pressure points and improve comfort of the syringe 400 during use.

In various embodiments, the syringe 400 comprises a needle 41 with a gauge, stiffness, bevel and length to facilitate penetration of the outer layer of the eye, namely the cornea, just slightly entering the anterior chamber, minimizing the risk of contacting other intraocular structures.

In various embodiments, during use, the syringe 400 is advanced so that the needle 41 penetrates the outer layer of the eye, (i.e. the cornea), and enters the anterior chamber of the eye. After the needle 41 penetrates the outer layer of the eye, (i.e. the cornea), and its tip is positioned within the anterior chamber, pressure is applied to the grips 46, 47 in the direction of the arrows 49. Applying said pressure moves grips 46, 47 closer to each other (i.e. compresses the handle 45), and advances the plunger 43 and the plunger seal 42 forwardly within the barrel 44, toward the needle 41. The forward movement of the plunger 43 and the plunger seal 42 toward the needle 41 generates positive pressure in the barrel 44, and injects fluid from the barrel 44 into the anterior chamber of the eye.

In some embodiments, contact with the outer surface of the barrel 44 prevents further movement of the grips 46, 47 in the direction of the arrows 49. In other embodiments, some other mechanical limiter, for example the stopper 20, can limit the movement of the grips 46, 47. This safe stop feature of the syringe 400 allows an operator to perform a procedure without an assistant or direct visualization of withdrawn liquid. Another way to predetermine the amount of fluid injected by the syringe 400 is by adjusting the angle Θ, formed between the handle 45 and the barrel 44, i.e., increasing the angle Θ will result in a greater distance between the grips 46, 47, and a larger volume of fluid is able to be ejected from the barrel 44 during use of the syringe 400.

Figure 5:
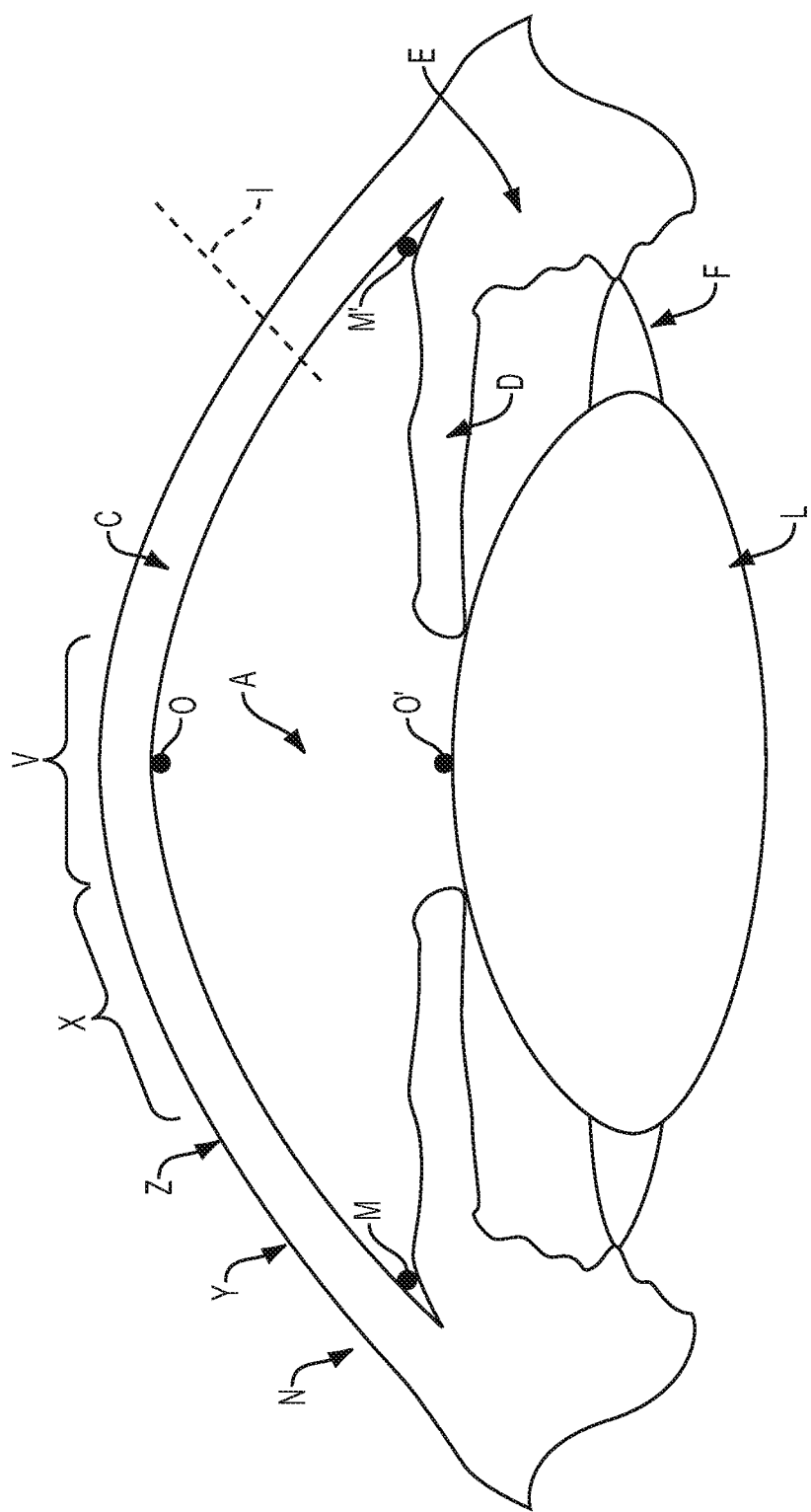
FIG. 5 illustrates an anterior-posterior cross section through the anterior chamber of an exemplary human eye.

FIG. 5 illustrates an anterior-posterior cross section through the anterior chamber of a human eye. The cornea C is a clear window into the anterior chamber A. The dimensions of the anterior chamber A are approximately 3 mm deep at the height of the dome of the cornea C, a distance defined as the length from point O to point O', and 12.5 mm wide, a distance defined as the length from point M to point M'. The anterior chamber A is the space formed between the posterior edge of the cornea C in the front, and the anterior edge of the lens L and the iris D in the back. The pupil is the opening in the iris D.

Further, the lens L is suspended in the middle of the eye with zonules F. These zonules are fibers that are anchored at the ciliary body E. The limbus is the transition zone between the white part of the eye, the sclera, and the cornea. The limbus is composed of two zones, the 1 mm white zone, which is the section of the limbus between the posterior limbal border N, and the mid-limbal line Y; and a 1 mm blue zone, between the mid-limbal line Y and the anterior limbal border Z. The visual axis V is a zone in the central cornea approximately 3-4 mm wide. While in a conventional anterior chamber paracentesis or intracameral injection procedure the needle may be inserted only at the limbus, the devices taught herein allow for safe expansion of the needle insertion zone to include injector zone X, between the anterior limbal border Z and the edge of the visual axis V, and even to include the visual axis V if deemed medically necessary, e.g., in rare circumstances such as severe peripheral corneal scarring it may be necessary to access the anterior chamber through visual axis V. Axis I shows the direction and angle of penetration into the anterior chamber using the approaches taught herein.

Figure 6:
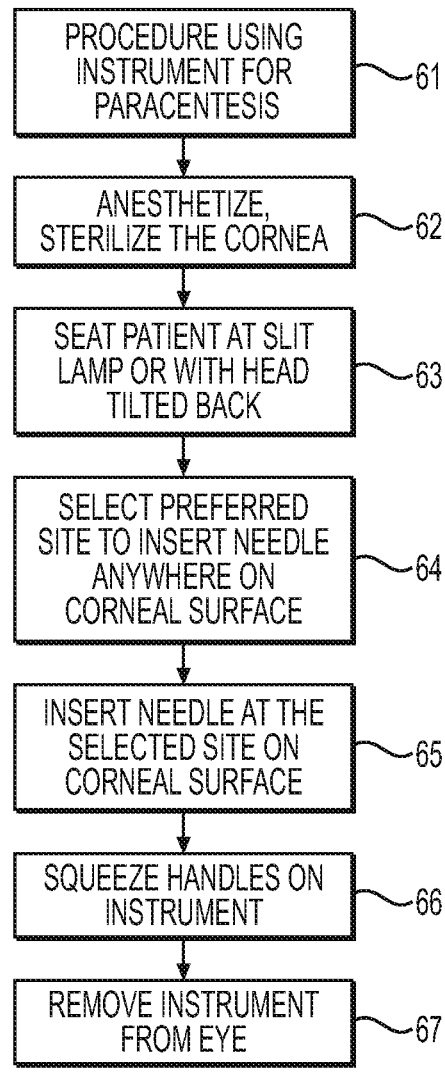
FIG. 6 illustrates an exemplary method describing the anterior chamber paracentesis or intracameral injection procedure using the devices taught herein.

FIG. 6 illustrates an exemplary method describing the anterior chamber paracentesis or intracameral injection procedure using the devices taught herein. At Step 61, the method in general is described as a procedure for using an instrument for paracentesis for example syringes 100, 200, 300, or 400. In Step 62, the surgical site is prepared, which includes anesthetizing and sterilizing the cornea. In Step 63, the patient is positioned so as to be at a slit lamp or is seated in the exam chair or on a procedure table with their head titled backward. In Step 64, a preferred site to insert the needle of the paracentesis device on the corneal surface is selected. In Step 65, the needle is inserted at the selected site on the corneal surface. In Step 66, the handles, for example the handles 15, 25, 35, or 45 are squeezed (i.e. compressed). In Step 67, the instrument is removed from the eye. Variations of this method will be obvious to a person of ordinary skill in the art, and are encompassed by the present disclosure.

FIG. 7A illustrates a plan view of another embodiment of a syringe 700A, according to various embodiments of the present disclosure. As is depicted in FIG. 7A, the syringe 700A in this embodiment uses a luer-type syringe 71, which includes a luer connector 72 enabling interchangeable luer-compatible needles or other luer-compatible devices, to be attached to the end of the syringe 71. The syringe 700A also includes a barrel 74 and a plunger extension 73 coupled to a plunger 76 and a plunger seal (not shown) positioned at least partially within the barrel 74. According to various embodiments, the syringe 700A includes first handles 75A, 75B having a first length, and second handles 75C, 75D having a second length, wherein the first length is longer than the second length. Handles of different lengths, as illustrated in the syringe 700A of FIG. 7, take advantage of the lever principle, which can be advantageous for procedures performed using the presently-disclosed device.

In some embodiments, the first handles 75A, 75B are flexibly connected at, or near, the plunger extension 73 at one end, and at, or near, the second handles 75C, 75D at another end. In other embodiments, the second handles 75C, 75D are flexibly connected at, or near, the first handles 75A, 75B at one end, and at or near, the barrel 74 at another end. The first handles 75A, 75B, the second handles 75C, 75D, and their connections to one another and/or to other structures may be configured to enable manipulation of the plunger extension 73, while remaining sufficiently flexible to be compressed in the direction of the arrows 79.

The first handles 75A, 75B, and the second handles 75C, 75D can connect to one another, to the plunger extension 73 and the barrel 74 in a variety of ways. For example, the first handles 75A, 75B, and the second handles 75C, 75D may include living hinges, pin joints, spring hinges, or the like. Alternatively, the first handles 75A, 75B, and the second handles 75C, 75D can connect to one another, to the plunger extension 73, and the barrel 74 using a variety of chemical means, including various adhesives, epoxies, welding, or the like. Additionally, in various embodiments, the first handles 75A, 75B, the second handles 75C, 75D, the plunger extension 73, and the barrel 74 may comprise a single, injection-molded component.

In some embodiments, the first handles 75A, 75B, and the second handles 75C, 75D are disposed in diametrical opposition about the barrel 74 and the plunger extension 73. The first handles 75A, 75B, and the second handles 75C, 75D may be provided in a variety of materials, including, but not limited to, various metals, composite materials, and plastics, such as polyethylene, polypropylene, or polyvinyl chloride.

In some embodiments, the first handles 75A, 75B are ergonomically designed to provide a comfortable resting surface for the operator's fingers. Two fingers can be placed on the first handles 75A, 75B. The remaining fingers of the operator can rest at multiple points along the syringe 700A. The additional contact points may be used to improve control of the syringe 700A and to stabilize the syringe 700A within the hand of the operator. In some embodiments, a user may position their remaining fingers on the plunger extension 73 and/or the barrel 74.

In various embodiments, the syringe 700A can be configured such that the maximum distance that the first handles 75A, 75B, and the second handles 75C, 75D can be compressed corresponds to a certain volume of withdrawn fluid. In some embodiments, contact with the outer surface of the barrel 74 prevents further compression of the first handles 75A, 75B, and the second handles 75C, 75D. In other embodiments, some other mechanical limiter, such as the stopper 20, can limit the distance that the first handles 75A, 75B, and the second handles 75C, 75D can be compressed. This safe stop feature of the syringe 700A allows an operator to use the syringe 700A without an assistant or direct visualization of the withdrawn liquid.

In some embodiments, the maximum volume of withdrawn fluid is adjusted by changing the angle of the first handles 75A, 75B, and the second handles 75C, 75D relative to the barrel 74. For example, increasing the angle of the first handles 75A, 75B, and the second handles 75C, 75D relative to the barrel 74 increases the distance by which they can be compressed. The larger compression distance allows the plunger 76, and the plunger seal (not shown) to be retracted further within the barrel 74, rearwardly from the luer connector 72, thereby increasing the volume of fluid able to be withdrawn using syringe 700A. Conversely, a smaller angle of the first handles 75A, 75B, and the second handles 75C, 75D relative to the barrel 74 results in a shorter distance by which they can be compressed. This smaller compression distance limits the distance the plunger 76, and the plunger seal (not shown) can be retracted within the barrel 74, rearwardly from the luer connector 72, thereby decreasing the volume of fluid able to be withdrawn using the syringe 700A.

In some embodiments, pressure is applied on the first handles 75A, 75B in the direction of the arrows 78. This action can advance the syringe 700A and drive a needle through bodily tissue, such as the cornea, into the anterior chamber of a patient's eye. The design of the first handles 75A, 75B, combined with friction forces between the plunger seal (not shown) and the inside wall of the barrel 74, allows a user to apply a sufficient pressure on the first handles 75A, 75B to penetrate the cornea, without activating the plunger extension 73.

The maximum force applied on the first handles 75A, 75B before resulting in movement of the plunger extension 73 can allow a user to safely manipulate and position the syringe 700A device, for example, within the anterior chamber of a human eye. The maximum force applied on the first handles 75A, 75B before resulting in movement of the plunger extension 73 can be about, more than, or less than 50, 100, 150, 200, 250, 300, 350, 400, 420, 440, 460, 480, 500, 520, 540, 560, 580, 600, 650, 700, 750 or 800 grams-force (gf). These values can be used to define discrete forces, such as 480 or 500 gf. These values can also be used to define a range of forces, such as from about 460 to 520 gf.

Once the needle has penetrated the outer layer of the eye, (i.e. the cornea), and the needle tip is within the anterior chamber, pressure can then be applied on the first handles 75A, 75B in the direction of the arrows 79, causing the first handles 75A, 75C, and the second handles 75B, 75D to compress and straighten, pulling the plunger extension 73, the plunger 76 and the plunger seal (not shown) rearwardly away from the needle. The rearward movement of the plunger extension 73, the plunger 76, and the plunger seal (not shown) generates negative pressure in the barrel 74, drawing fluid from the anterior chamber of the eye into the barrel 74.

In various embodiments, devices of the present disclosure may be provided in either single-use or reusable configurations. For example, in some embodiments, single-use paracentesis devices may be provided. Additionally, the devices of the present disclosure may be provided in reusable configurations that can be sterilized between uses and might provide added value to hospitals or treatment facilities.

FIGS. 7B-7F illustrate other embodiments of the syringe 700A. The other embodiments are referred to as syringe 700B-700F. To facilitate explanation, like reference numbers are used in FIGS. 7A-7F.

Figure 7C:
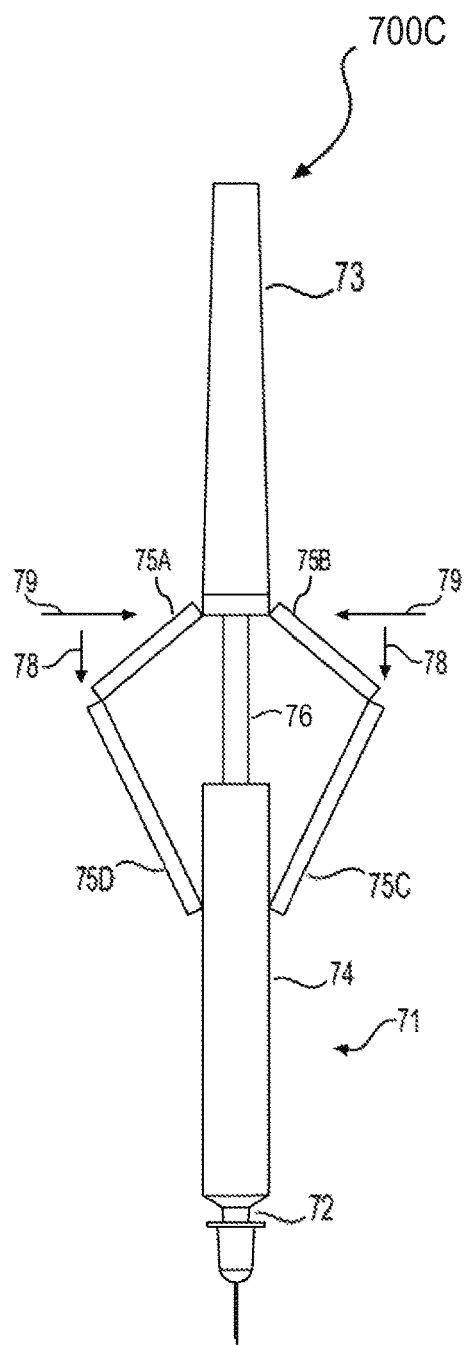

FIGS. 7A-7C illustrate a syringe 700 as taught herein that includes the plunger extension and different structural arrangements of the handles 75A-75D.

Figure 7D:
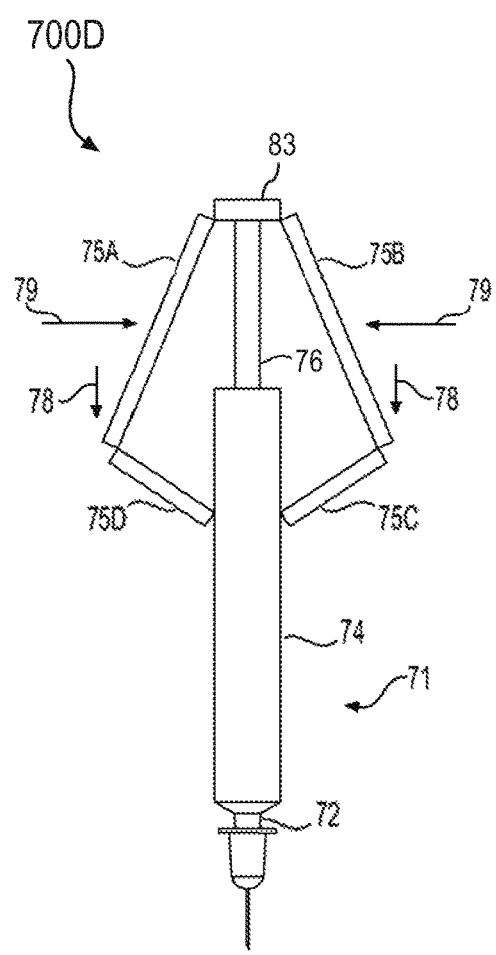
Figure 7E:
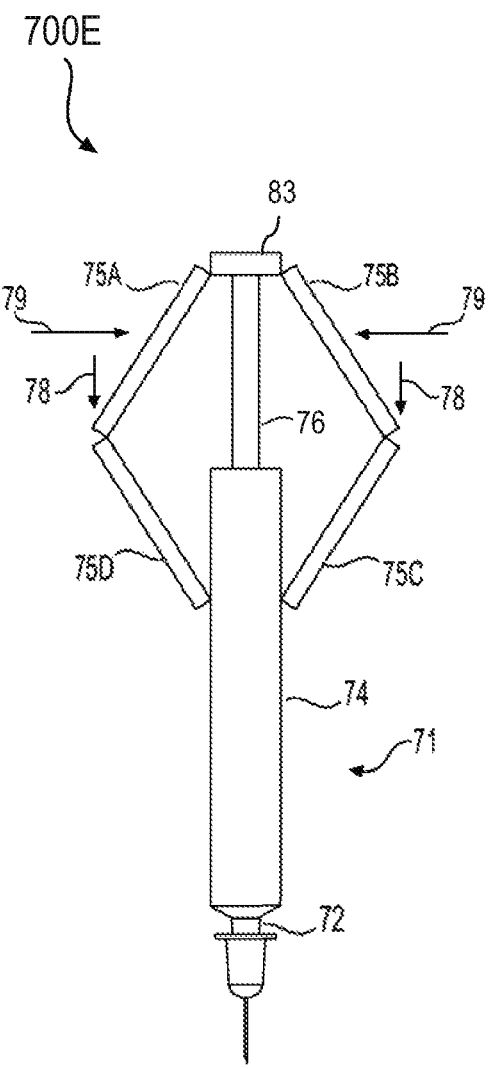
Figure 7F:
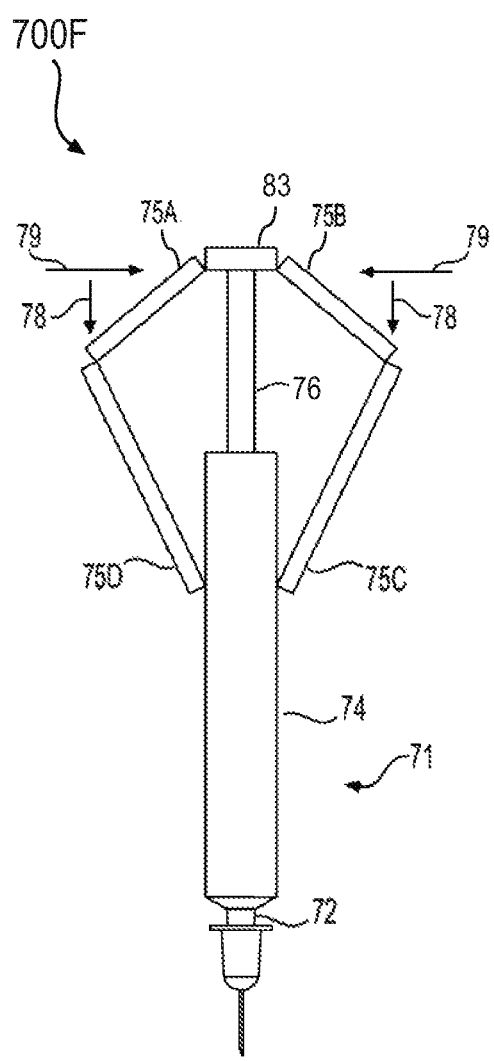

FIGS. 7D-7F illustrate a syringe 700 as taught herein without the plunger extension and different structural arrangements of the handles 75A-75D.

FIG. 7B illustrates syringe 700B, according to various embodiments of the present disclosure having the first handles 75A, 75B, and the second handles 75C, 75D of equal length.

FIG. 7C illustrates syringe 700C, according to various embodiments of the present disclosure. The syringe 700C includes the first handles 75A, 75B having a first length, and the second handles 75C, 75D having a second length, wherein the first length is shorter than the second length.

FIGS. 7A-7C also illustrate different attachment points of the handles 75A-75D with respect to the syringe barrel and the plunger.

FIGS. 7D-7F illustrate syringes 700D, 700E, 700F having plunger flanges 83, and do not include the plunger extensions as illustrated in FIGS. 7A-7C.

FIG. 7D illustrates syringe 700D including the plunger flange 83 and the first handles 75A, 75B having a first length, and the second handles 75C, 75D having a second length, wherein the first length is longer than the second length.

FIG. 7E illustrates syringe 700E including the plunger flange 83 and the first handles 75A, 75B having a first length, and the second handles 75C, 75D having a second length, wherein the first length is equal to the second length.

FIG. 7F illustrates syringe 700F including the plunger flange 83 and the first handles 75A, 75B having a first length, and the second handles 75C, 75D having a second length, wherein the first length is shorter than the second length.

Figure 8A:
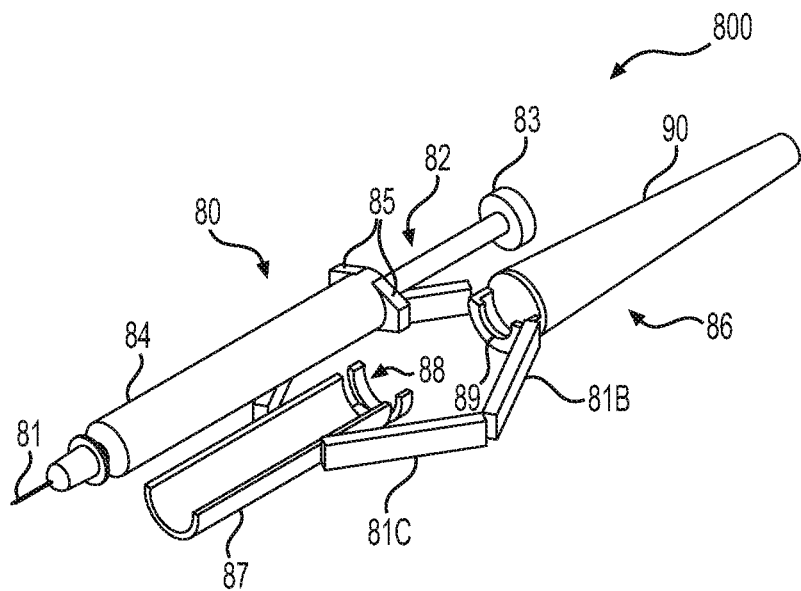
FIG. 8A illustrates a device including a syringe holder system, according to various embodiments of the present disclosure.

FIG. 8A illustrates an embodiment of a device including a syringe holder system 800, according to various embodiments of the present disclosure. In various embodiments, a conventional syringe 80 can be used with an embodiment of the presently disclosed device. For example, the conventional syringe 80 can be loaded into a syringe holder 86. In various embodiments, the syringe holder 86 comprises a syringe barrel carrier 87, a plunger extension 90, a barrel fixation means 88, a plunger fixation means 89, and handles 81A (not labelled), 81B, 81C, and 81D (not labelled). The syringe holder 86 may be configured to securely contain the conventional syringe 80.

In various embodiments, the conventional syringe 80 comprises a needle 81, a barrel 84, barrel flanges 85, a plunger 82, and a plunger flange 83 in various configurations. For example, the barrel 84 of the conventional syringe 80 includes the needle 81 at, or near, one end thereof, and the barrel flanges 85 at, or near, another end thereof. Also, the conventional syringe 80 can include the plunger 82 disposed as least partially within the barrel 84. The plunger 82 can include the plunger flange 83 at, or near, the end of the plunger 82 that is not disposed within the barrel 84.

In various embodiments, the conventional syringe 80 fits securely within syringe holder 86. In some embodiments, the barrel 84 rests within the syringe barrel carrier 87 such that the barrel flanges 85 align with, and secure into the barrel fixation means 88. In various embodiments, the barrel fixation means 88 includes a channel, or semicircular notch within the syringe barrel carrier 87 configured to contain the barrel flange 83 therein.

Additionally, when the barrel 84 rests within the syringe barrel carrier 87, the plunger flange 83 will be aligned with, and inserted into the plunger fixation means 89. In various embodiments, the plunger fixation means 89 is disposed on, or near, the end of the plunger extension 90 most proximate the syringe barrel carrier 87. In some embodiments, the plunger fixation means 89 comprises a hollow, semicircular structure configured to receive the plunger flange 83.

For example, the barrel fixation means 88 and the plunger fixation means 89 can be provided in a variety of configurations that can accommodate the plunger flange 83, and the barrel flanges 85, respectively. In some embodiments, for example, the barrel fixation means 88, and the plunger fixation means 89 are sized and shaped such that they achieve a press-fit connection with their respective flanges 85, 83.

Additionally, various mechanical or chemical means may be provided to secure the conventional syringe 80 to the syringe holder 86. For example, various buckles, clasps, ties, straps, adhesives, or the like can be used to connect the conventional syringe 80 to the syringe holder 86. In some embodiments, the syringe holder 86 provides a more cost-effective solution for health care providers to redeem the benefits of the presently disclosed devices.

In some embodiments, extended the plunger extension 90 provides an improved balance and center of gravity of the syringe holder 86. In various embodiments, the handles 81A (not labelled), 81B, 81C, and 81D (not labelled) are provided in a variety of lengths, widths, and surface geometries. For example, the handles 81A (not labelled), 81B, 81C, and 81D (not labelled) can be the same length, can vary in length, can provide wide finger rests for increased user comfort, and can include ergonomic contours to reduce pressure points and improve comfort of the syringe holder 86 during use.

Further, a variety of materials can be used to comprise the syringe holder 86. For example, the syringe holder 86 can comprise at least one of a metal, plastic, polymer, silicone, or other material or combination of materials with adequate rigidity/flexibility to successfully inject and aspirate fluid in accordance with the presently disclosed devices and methods. Further, the syringe holder 86 may comprise multiple components, or may be formed using a mechanical process, such as injection molding, to provide the syringe holder 86 as a single piece of material.

In some embodiments, during use of the syringe holder system 800, the syringe 80 is loaded into the syringe holder 86. In some embodiments, a user positions their fingers on the handles 81A (not labelled), 81B and positions their remaining fingers on any other surface of the syringe holder system 800. The operator can then advance the tip of the needle 81 into some region of the patient, for example, the anterior chamber of the eye. Pressure is then applied to the handles 81A (not labelled), 81B so that they move closer to each other (i.e. the handles 81A (not labelled), 81B, 81C, 81D (not labelled) are compressed).

As a result, since the handles 81A (not labelled), 81B, 81C, 81D (not labelled) are coupled to the plunger extension 90 and the plunger seal (not shown), which can move freely within the barrel 84, the action of compressing the handles 81A (not labelled), 81B causes the handles 81A (not labelled), 81B, 81C, 81D (not labelled) to straighten, withdrawing the plunger extension 90, the plunger (not shown), and the plunger seal (not shown) rearwardly, away from the needle 81. In turn, the plunger (not shown), and the plunger seal (not shown) extend further out of the barrel 84, and the plunger seal (not shown) moves closer to the open end of the barrel 84, generating negative pressure in the barrel 84 to draw out fluid from the anterior chamber of the eye into the barrel 84.

In various embodiments, the syringe holder system 800 can be configured such that the maximum distance that the handles 81A (not labelled), 81B, 81C, 81D (not labelled) can be compressed corresponds to a certain volume of withdrawn fluid. In some embodiments, the handles 81A (not labelled), 81B, 81C, 81D (not labelled) are prevented from compressing further by contact with the outer surface of the barrel 84. In other embodiments, some other mechanical limiter, such as the stopper 20, can limit the movement of the handles 81A (not labelled), 81B, 81C, 81D (not labelled). This safe stop feature of the syringe holder system 800 allows an operator to use the syringe holder system 800 without an assistant or direct visualization of the withdrawn liquid.

In some embodiments, the maximum volume of withdrawn fluid is adjusted by changing the angle of the handles 81A (not labelled), 81B, 81C, 81D (not labelled) relative to the barrel 84. For example, increasing said angle increases the distance the handles 81A (not labelled), 81B, 81C, 81D (not labelled) can be compressed, which allows the plunger (not shown) to be retracted further within the barrel 84, thereby increasing the volume of fluid able to be withdrawn using the syringe holder system 800. Conversely, a smaller angle of the handles 81A (not labelled), 81B, 81C, 81D (not labelled) relative to the barrel 84 results in a shorter distance that the handles 81A (not labelled), 81B, 81C, 81D (not labelled) can be compressed, limiting the distance the plunger (not shown) can be retracted within the barrel 84, thereby decreasing the volume of fluid able to be withdrawn using the syringe holder system 800.

Figure 8B:
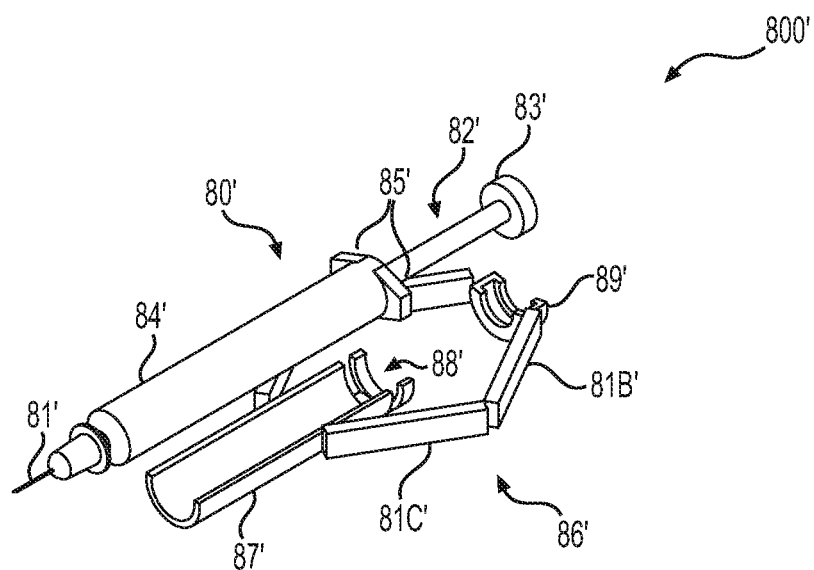
FIG. 8B illustrates another a device including a syringe holder system, according to various embodiments of the present disclosure.

FIG. 8B illustrates another embodiment of a device including a syringe holder system 800, according to various embodiments of the present disclosure. In various embodiments, a conventional syringe 80' can be used with an embodiment of the presently disclosed device. For example, the conventional syringe 80' can be loaded into a syringe holder 86'. In various embodiments, the syringe holder 86' comprises a syringe barrel carrier 87', a barrel fixation means 88', a plunger fixation means 89', and handles 81A' (not labelled), 81B', 81C', and 81D' (not labelled). The syringe holder 86' may be configured to securely contain the conventional syringe 80.

In various embodiments, the conventional syringe 80' comprises a needle 81', a barrel 84', barrel flanges 85', a plunger 82', and a plunger flange 83' in various configurations. For example, the barrel 84' of the conventional syringe 80' includes the needle 81' at, or near, one end thereof, and the barrel flanges 85' at, or near, another end thereof. Also, the conventional syringe 80' can include the plunger 82' disposed as least partially within the barrel 84'. The plunger 82' can include the plunger flange 83' at, or near, the end of the plunger 82' that is not disposed within the barrel 84'.

In various embodiments, the conventional syringe 80' fits securely within syringe holder 86'. In some embodiments, the barrel 84' rests within the syringe barrel carrier 87' such that the barrel flanges 85' align with, and secure into the barrel fixation means 88'. In various embodiments, the barrel fixation means 88' includes a channel, or semicircular notch within the syringe barrel carrier 87' configured to contain the barrel flange 83' therein.

Additionally, when the barrel 84' rests within the syringe barrel carrier 87', the plunger flange 83 will be aligned with, and inserted into the plunger fixation means 89. In various embodiments, the plunger fixation means 89 is disposed on, or near, and one end of the handles 81A' (not labelled), 81B'. In some embodiments, the plunger fixation means 89' comprises a hollow, semicircular structure configured to receive the plunger flange 83'.

For example, the barrel fixation means 88' and the plunger fixation means 89' can be provided in a variety of configurations that can accommodate the plunger flange 83', and the barrel flanges 85', respectively. In some embodiments, for example, the barrel fixation means 88', and the plunger fixation means 89' are sized and shaped such that they achieve a press-fit connection with their respective flanges 85', 83'.

Additionally, various mechanical or chemical means may be provided to secure the conventional syringe 80' to the syringe holder 86'. For example, various buckles, clasps, ties, straps, adhesives, or the like can be used to connect the conventional syringe 80' to the syringe holder 86'. In some embodiments, the syringe holder 86' provides a more cost-effective solution for health care providers to redeem the benefits of the presently disclosed devices.

In various embodiments, the handles 81A' (not labelled), 81B', 81C', and 81D' (not labelled) are provided in a variety of lengths, widths, and surface geometries. For example, the handles 81A' (not labelled), 81B', 81C', and 81D' (not labelled) can be the same length, can vary in length, can provide wide finger rests for increased user comfort, and can include ergonomic contours to reduce pressure points and improve comfort of the syringe holder system 800 during use.

Further, a variety of materials can be used to comprise the syringe holder 86'. For example, the syringe holder 86' can comprise at least one of a metal, plastic, polymer, silicone, or other material or combination of materials with adequate rigidity/flexibility to successfully inject and aspirate fluid in accordance with the presently disclosed devices and methods. Further, the syringe holder 86' may comprise multiple components, or may be formed using a mechanical process, such as injection molding, to provide the syringe holder 86' as a single piece of material.

In some embodiments, during use of the syringe holder system 800', the conventional syringe 80' is loaded into the syringe holder 86'. In some embodiments, a user positions their fingers on the handles 81A' (not labelled), 81B' and positions their remaining fingers on any other surface of the syringe holder system 800'. The operator can then advance the tip of the needle 81' into some region of the patient, for example, the anterior chamber of the eye. Pressure is then applied to the handles 81A' (not labelled), 81B' so that they move closer to each other (i.e. the handles 81A (not labelled), 81B, 81C, 81D (not labelled) are compressed).

As a result, since the plunger 82' is attached to the handles 81A' (not shown), 81B', via the plunger fixation means 89', the action of compressing the handles 81A (not labelled), 81B causes the handles 81A (not labelled), 81B, 81C, 81D (not labelled) to straighten, withdrawing the plunger (not shown), and the plunger seal (not shown) rearwardly, away from the needle 81'. In turn, the plunger (not shown), and the plunger seal (not shown) extend further out of the barrel 84', and the plunger seal (not shown) moves closer to the open end of the barrel 84', generating negative pressure in the barrel 84' to draw out fluid from the anterior chamber of the eye into the barrel 84'.

In various embodiments, the syringe holder system 800' can be configured such that the maximum distance that the handles 81A' (not labelled), 81B', 81C', 81D' (not labelled) can be compressed corresponds to a certain volume of withdrawn fluid. In some embodiments, the handles 81A' (not labelled), 81B', 81C', 81D' (not labelled) are prevented from compressing further by contact with the outer surface of the barrel 84'. In other embodiments, some other mechanical limiter, such as the stopper 20, can limit the compression of the handles 81A' (not labelled), 81B', 81C', 81D' (not labelled). This safe stop feature of the syringe holder system 800' allows an operator to use the syringe holder system 800' without an assistant or direct visualization of the withdrawn liquid.

In some embodiments, the maximum volume of withdrawn fluid is adjusted by changing the angle of the handles 81A' (not labelled), 81B', 81C', 81D' (not labelled) relative to the barrel 84'. For example, increasing said angle increases the distance the handles 81A' (not labelled), 81B', 81C', 81D' (not labelled) can be compressed, allows the plunger (not shown) to be retracted further within the barrel 84', thereby increasing the volume of fluid able to be withdrawn using the syringe holder system 800'. Conversely, a smaller angle of the handles 81A' (not labelled), 81B', 81C', 81D' (not labelled) relative to the barrel 84' results in a shorter distance that the handles 81A' (not labelled), 81B', 81C', 81D' (not labelled) can be compressed, limiting the distance the plunger (not shown) can be retracted within the barrel 84', thereby decreasing the volume of fluid able to be withdrawn using the syringe holder system 800'.

The embodiments of the disclosed paracentesis device provide a number of advantages over current devices and methods. A differentiating feature of the presently disclosed device is that it is ergonomically designed for optimal grip, contact area, and manipulation. Further, the presently disclosed device may comprise a barrel including gradation marks to precisely indicate even small volumes of fluid. Additionally, the presently disclosed devices provide for the aspiration of a predetermined amount of fluid using variety of means, including, but not limited to mechanical devices, such as stopper 20.

Additionally, the devices of the present disclosure can allow for a controlled rate of aspiration. A controlled aspiration rate can reduce potential damage to surrounding tissue during the paracentesis procedure. A further differentiating feature of the presently disclosed device is that the inner lining of the syringe barrel may be coated with materials beneficial for storing a particular fluid. A yet further differentiating feature of the presently disclosed device is that, in some embodiments, it does not require a separate aspirating device to create negative pressure or suction.

While this design in any of its embodiments can be used in a conventional paracentesis procedure of the anterior chamber, a yet further differentiating feature is that, in any of its embodiments, the needle length provides the surgeon with more flexibility in selecting the safest possible location on the cornea to access the chamber in a given patient. Thus, the paracentesis or injection devices of the embodiments taught herein are safer and easier to control than conventional apparatuses.

The foregoing description of example embodiments of the invention provides illustration and description, but is not intended to be exhaustive or to limit the invention to the precise form disclosed. Modifications and variations are possible in light of the above teachings or may be acquired from practice of the invention. For example, while a series of acts has been described, the order of the acts may be modified in other implementations consistent with the principles of the invention. Further, non-dependent acts may be performed in parallel.

It should be appreciated that the various embodiments individually described herein may be practiced in combination in certain circumstances without departing from the scope of the present invention. Other embodiments will be apparent to those skilled in the art from consideration of the specification and practice of this disclosure. It is intended that the specification and examples be considered as exemplary only, with the true scope and spirit of the disclosed devices and methods being indicated by the claims.

What is claimed is:

1. An aspirating syringe having a distal end for insertion into a cavity and a proximal end operable by a user comprising:
    a syringe barrel having a distal end couplable to a needle and an open proximal end;
    a plunger seal disposed inside the syringe barrel;
    a plunger rod disposed in the syringe barrel extending along a longitudinal axis between a first end coupled to the plunger seal and a second end opposite of the first end;
    a plunger extension coupled to the second end of the plunger rod moving in unison with the plunger rod, the plunger extension having an elongated tapered cylinder body extending longitudinally from the second end of the plunger rod;
    a compressible handle having a plurality of components, the plurality of components forming a first linked handle and a second linked handle disposed symmetrically in diametrical opposition about the barrel and the plunger rod;
    the first linked handle having a first handle and a second handle, the first handle having a first length and the second handle having a second length different from the first length, the first handle having a proximal end flexibly coupled to the plunger extension and a distal end flexibly coupled to a proximal end of the second handle, and the second handle having a distal end flexibly coupled to a portion of the syringe barrel;
    the second linked handle having a first handle and a second handle, the first handle having a first length and the second handle having a second length different from the first length, the first handle having a proximal end flexibly coupled to the plunger extension and a distal end flexibly coupled to a proximal end of the second handle, and the second handle having a distal end flexibly coupled to a portion of the syringe barrel;
    wherein compressing the compressible handle causes the handle to longitudinally extend and causes the syringe plunger to move rearwardly in the syringe barrel away from the needle.

2. The syringe of claim 1, wherein the first handle and second handle of the first linked handle are connected to each other by one of a living hinge, a pin joint, or a spring hinge.

3. The syringe of claim 1, wherein the first handle and second handle of the second linked handle are connected to each other by one of a living hinge, a pin joint, or a spring hinge.

4. The syringe of claim 1, wherein the distal end of the second handles are directly coupled to the portion of the syringe barrel.

5. The syringe of claim 1, wherein the plunger extension stabilizes the syringe in a hand of the user.

6. The syringe of claim 1, wherein the plunger extension provides an improved balance and center of gravity for the syringe.

7. The syringe of claim 1, further comprising a limiter to limit movement of the compressible handle to a desired distance, the desired distance corresponding to an aspirated volume of fluid.

* * * * *